US012606678B2

(12) United States Patent (10) Patent No.: US 12,606,678 B2
Farajollahi et al. (45) Date of Patent: Apr. 21, 2026

(54) COMPLEXATED BIOMOLECULES FOR USE IN CONTAMINATED SOIL OR GROUNDWATER CLEANUP

(71) Applicant: BlueHalo, LLC, Huntsville, AL (US)

(72) Inventors: Sanaz Farajollahi, Mason, OH (US); Patrick B. Dennis, Loveland, OH (US); Rajesh R. Naik, Huntsville, AL (US); Joseph M. Slocik, Huntsville, AL (US); Nancy Kelley-Loughnane, Cincinnati, OH (US)

(73) Assignee: BlueHalo, LLC, Northwest, AL (US)

( * ) Notice: Subject to any disclaimer, the term of this patent is extended or adjusted under 35 U.S.C. 154(b) by 264 days.

(21) Appl. No.: 18/311,419

(22) Filed: May 3, 2023

(65) Prior Publication Data

US 2023/0357514 A1     Nov. 9, 2023

Related U.S. Application Data

(60) Provisional application No. 63/337,658, filed on May 3, 2022.

(51) Int. Cl.
| | |
|---|---|
| *C08H 1/00* | (2006.01) |
| *B09C 1/08* | (2006.01) |
| *C02F 1/28* | (2023.01) |
| *C07K 14/435* | (2006.01) |
| *C09K 17/32* | (2006.01) |
| *C02F 103/06* | (2006.01) |

(52) U.S. Cl.
CPC ................ *C08H 1/00* (2013.01); *B09C 1/08* (2013.01); *C02F 1/285* (2013.01); *C07K*

14/43536 (2013.01); *C09K 17/32* (2013.01); *C02F 2103/06* (2013.01); *C02F 2305/04* (2013.01)

(58) Field of Classification Search
None
See application file for complete search history.

(56) References Cited

FOREIGN PATENT DOCUMENTS

| | | | | |
|---|---|---|---|---|
| CA | 3074593 A1 | * | 3/2019 | ..... C12Y 301/08001 |
| CN | 101277972 A | * | 10/2008 | .......... A23L 33/185 |

OTHER PUBLICATIONS

Alshabib, et al. Water Air Soil Pollut (2020) 231: 428. (Year: 2010).*
Machine translation of CN-101277972-A, pp. 1-11. (Year: 2008).*
Shulevich, et al. Separation and Purification Technology 113 (2013) 18-23. (Year: 2013).*
Hernandez, et al. Environ. Sci.: Water Res. Technol., 2022, 8, 1188. (Year: 2022).*
Zaiee, et al. Substantia. An International Journal of the History of Chemistry 4(2) Suppl.: 79-88, 2020. (Year: 2020).*

(Continued)

*Primary Examiner* — Clare M Perrin
(74) *Attorney, Agent, or Firm* — Goodwin Procter LLP

(57) ABSTRACT

A polyelectrolyte-surfactant complex, a method of removing a toxic substance from contaminated soil or contaminated groundwater using a polyelectrolyte-surfactant complex and a method of making a polyelectrolyte-surfactant complex. The polyelectrolyte-surfactant complex is made from a complexated recombinant intrinsically disordered protein that has been electrostatically conjugated to an anionic surfactant to provide enhanced liquid-liquid phase separation properties.

15 Claims, 10 Drawing Sheets

(56) References Cited

OTHER PUBLICATIONS

Faller, et al. Acc. Chem. Res. 2014, 47, 2252-2259. (Year: 2014).*
McCaslin, et al. Nature Scientific Reports, (2019) 9:17303. (Year: 2019).*
Gupta et al; Programmable mechanical properties from a worm jaw-derived biopolymer through hierarchical ion exposure; ACS Appl. Mater. Interfaces 2018.
Chau et al; Ion effect and metal-coordinated crosslinking for multiscale design of Nereis jaw inspired mechanomutable materials; ACS Nano. 2017.
Broomell et al; Critical role of zinc in hardening of Nereis jaws; Journal of Experimental Biology, 2006.
Slocik et al; Creation of energetic biothermite inks using ferritin liquid protein; Nature Communication 2017.

* cited by examiner

Nvjp1 Amino Acid Sequence

| | |
|---|---|
| Glycine | 36% |
| Basic (H, R, K) | 30% |
| Acidic (D, E) | 9.4% |
| Tyrosine | 7.3% |

Cationized protein          Anionic Surfactant

Nvjp1          Alkyl Ether Sulfonate          Nvjp-1-AES Phase
Separation

Coomassie stained SDS-page gel

Time:      0h      12h

Mix & Spin down

COMPLEXATED BIOMOLECULES FOR USE IN CONTAMINATED SOIL OR GROUNDWATER CLEANUP

This application claims the benefit of U.S. Provisional Patent Application Ser. No. 63/337,658 that was filed on May 3, 2022 and entitled "COMPLEXATED BIOMOLECULES FOR USE IN CONTAMINATED SOIL OR GROUNDWATER CLEANUP".

STATEMENT REGARDING FEDERALLY SPONSORED RESEARCH OR DEVELOPMENT

The subject matter of the present disclosure was made with government support under Contract No. USAF/FA8650-15-D-5405 that was awarded by the US Air Force. The government has certain rights in such subject matter.

TECHNICAL FIELD

The present disclosure relates generally to biomolecule processing to produce new materials with tailorable properties, and more particularly to processing a biomolecule through a protein and surfactant complexation such that the resulting material may be used as an absorbent in a liquid-liquid phase separation operation to remove toxic material from contaminated soil and groundwater sites.

BACKGROUND

Intrinsically disordered proteins (IDPs) are abundant in nature. One such example is Nvjp-1, a histidine-rich IDP from the jaw of the marine sandworm, *Nereis virens*.

Polyfluoroalkyl and perfluoroalkyl substances (PFAS) and related halogenated substances are frequently used in the manufacture of various commercial products that require certain non-stick, hydrophobic, friction-reduction, fire-prevention or surface-protective properties. For example, PFAS figures prominently in non-stick cookware, as well as in fire-retardant spray foams. Once their usefulness has been exhausted, PFAS-containing articles are discarded, typically into a landfill (in the case of cookware, appliances or the like) or into soil or groundwater sites (in the case of foam runoff after a firefighting encounter). The removal of PFAS-containing products from such sites has proven to be difficult, in part because the strong and stable carbon-fluorine bonds present within such substances are not readily degraded by conventional oxidative or reductive methods, and made more complicated by their surfactant-like structure. While various in-ground or above-ground processes may be used that involve the introduction of reactive agents into the effected groundwater or soil, such agents—while breaking down the PFAS into something more benign—may themselves introduce harmful byproducts that further insult the affected area. Likewise, physical reactors that typically promote the capture or entrainment of aerosols, bubbles or other PFAS-containing byproducts involve complex setups that are expensive to install and operate. Moreover, while activated carbon adsorption and related methods may be used in the case of PFAS-contaminated groundwater, they merely transfer cause the PFAS to change form, such as from an aqueous-based media to a solid-based one that still must be disposed of, such as within the aforementioned landfill.

SUMMARY

The authors of the present disclosure have discovered that various structural and chemical properties of certain IDPs may be modulated though the introduction of binding agents. For example, various metal binding sites in proteins (including those based on—for example—calcium, copper, iron and zinc) form metalloproteins that can be used to promote or change various biological processes.

For example, these metalloproteins may form a coordination complex, where the protein is in the form of a ligand that surrounds the metallic center. In a particular form, the ligand is a polydentate that forms chelate complexes through a complexation process. The authors of the present disclosure have discovered that absorbents may be created that are based on protein and surfactant complexation. In particular, by promoting the complexation between a histidine-rich protein (such as Nvjp-1) and an anionic surfactant, a resulting stable coacervate forms through liquid-liquid phase separation, and that this complex may be used as an absorbent for the removal of contaminants from soil and water.

More particularly, the authors of the present disclosure have discovered that the resulting coacervate is useful in removing transition metals, nanoparticles and other inorganic materials, as well as for certain organic recalcitrant compounds such as PFAS. They have further discovered that such an absorbent may be used for bioleaching of rare earth elements as an environmentally-friendly alternative to traditional heap leaching and related metal extraction techniques. Moreover, they have discovered that the concentration of the enzymes may be adjusted to give it tailorable activity and turnover properties.

According to an aspect of the present disclosure, a method of removing a toxic substance from contaminated soil or contaminated groundwater is disclosed. The method includes receiving a polyelectrolyte-surfactant complex (PESC) that comprises a cationized protein that has been undergone electrostatic conjugation with an anionic surfactant such that the PESC possesses liquid-liquid phase separation (LLPS, also referred to herein as liquid-liquid two phase separation (LL2P)) properties. As such, the PESC has a first liquid and a second liquid such that a complexated protein is present in the first liquid in a greater concentration than in the second liquid. In addition, the PESC is combined with one or both of the contaminated soil and the contaminated groundwater such that the toxic substance contained therein preferentially concentrates in the coacervate within the first liquid while the second liquid remains predominantly in contact with the contaminated groundwater or soil. After that, the first liquid and toxic substance adhered thereto may be separated or otherwise removed from the second liquid.

In certain embodiments, the proteinaceous phase is formed by the placement or establishment of self-assembling proteins into a liquid phase in a solution, after which they undergo a phase transition by arranging them into a matrix. Such a phase is often referred to as a membraneless organelle (also referred to as a proteinaceous phase globule) such that it forms a cohesive particle grouping while being generally devoid of a lipid membrane to separate the grouping from adjacent cytoplasmic or nuclear liquid. IDPs (such as the Nvjp-1 disclosed herein) are protein components that are contained within the membraneless organelle. Based on the authors' understanding that under certain conditions, the weak multivalent attractive forces that are present between the proteins and the ribonucleic acid (RNA) within nuclear bodies such as membraneless organelles may cause such bodies to participate in LLPS in order to assemble increased IDP concentrations that in turn can function as a major component of the membraneless organelle. From this, the authors of the present disclosure believe that complexation of the recombinant protein with an anionic surfactant produces a two-phase compound that has the ability to remove contaminants (such as the aforementioned PFAS) that are present in soil or groundwater. Without wishing to be bound by theory, the authors of the present disclosure believe that the removal is through a combination of LLPS and absorption. Thus, while the coacervate cannot carry out degradation by itself, it can be used with accessory PFAS degrading agents, such as enzymes, metals and nanoparticles that may also be concentrated in the coacervate.

According to another aspect of the present disclosure, a method of making a PESC is disclosed. The method includes interacting a cationized protein (such as the histidine-rich IDP) with a surfactant. The resulting PESC is in the form of a membraneless organelle that has enhanced LLPS properties, including having the recombinant protein is present in a first liquid as a coacervate in a greater concentration than in the second liquid. Optionally, in terms of histidine-rich proteins, a metal cation can form a coordination with protein backbone to produce a metalized PESC.

According to yet another aspect of the present disclosure, a PESC is disclosed that includes a metalloprotein that comprises an IDP combined with a metal ion, as well as an anionic surfactant that is electrostatically conjugated to the metalloprotein such that the resulting PESC forms a membraneless organelle that has enhanced LLPS properties made up of a first liquid and a second liquid. In this way, the metalloprotein is present as a toxic substance remediation agent in the first liquid as a coacervate, and such coacervate is present in a greater concentration than in the second liquid. The toxic substance remediation agent is biodegradable.

BRIEF DESCRIPTION OF THE DRAWINGS

The embodiments set forth in the drawings are illustrative in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figures 1, 2A:
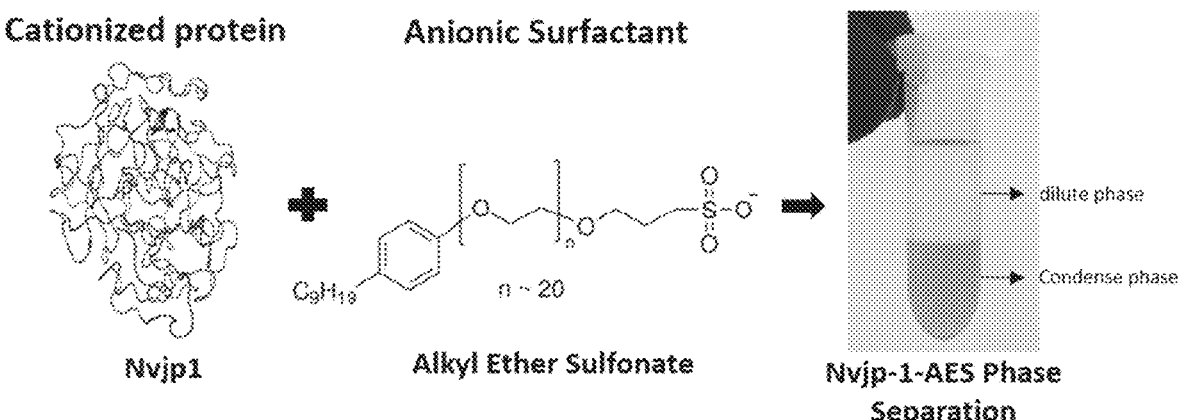
FIG. 1 depicts amino acid residues for the Nvjp-1 protein.
FIGS. 2A through 2C depict various biomaterial processing steps and test results associated with the formation of a two-phase Nvjp-1 and surfactant complex according to an aspect of the present disclosure.

A technical problem relates to how to perform cost-friendly environmental remediation of groundwater and soil that has been contaminated with toxic chemicals, including those containing PFAS and related agents. This technical problem further manifests itself in the way that traditional remediation approaches lack one or more figures of merit, including (i) the capacity to adhere or otherwise bind a remediation agent to the toxic material, (ii) preventing the remediation agent from introducing something into the affected area that might possess negative environmental externalities of its own, (iii) the ability to increase the activity of the remediation agent in the presence of an adsorbing or absorbing material and (iv) the ability have the remediation agent be easily and safely recycled and reused after degradation of the toxic material has been achieved or (in the alternative) be safely destroyed or biodegraded the latter of which includes substances that naturally break down into simpler, decomposed or lower-weight components in the presence of a bacteria or other living organism within a natural terrestrial or aqueous environment over the passage of a relatively short amount of time, typically within days, weeks or months rather than over the course of multiple years or more.

In this regard, aspects of the present disclosure provide a technical solution that improves these figures of merit through a new technique for creating a remediation agent through the processing of an IDP into a phase-separated system that can be applied to groundwater or soil for the removal of (among others) PFAS-based toxic materials. Significantly, a positive technical effect takes place when a recombinant protein is constructed by concatemerization of repetitive units within an IDP, leading to the formation of the PESC (which is also referred to as a complexated compound, complexated biomaterial, complexated biomolecule or the like) upon purification and complexation with a surfactant. The resulting PESC exhibits LLPS properties that are tailored to PFAS removal and degradation. Additionally, through this purification, the recombinant protein has more histidine compared to when it is in its natural state.

In one form, the remediation agent is formed as an absorbent to allow industrial sites, military installations, airports, wastewater treatment facilities, environmental cleanup sites and other areas that are in need of removal of PFAS-contaminated groundwater or soil without having to dig up the contaminated soil or perform complex groundwater washoffs, PFAS burning or other complex and risky procedures. In another form, if the remediation agent merely interacts with just one face of the contaminant rather than surrounding it completely, it may function as an adsorbent. In any event, the meaning will be apparent from the context.

For example, regarding waterborne contamination, the remediation agent may be applied to a wastewater treatment facility or groundwater site to permit the PESC that is present in the remediation agent to chemically react with the PFAS, after which the LLPS permits reclamation of the adhered pollutant or toxic material that is present at the bottom (that is to say, denser portion) of the wastewater. Following this, the enzymes or related accessory agents that were previously discussed may be introduced in order to degrade the PFAS. Once this occurs, the cationized protein (for example, Nvjp-1) can be reclaimed by precipitation in high salt and neutral pH followed by resolvation at low pH and reconjugation to alkyl ether sulfonate.

Referring first to FIG. 1, the starting protein, Nvjp-1, is rich in glycine, histidine, tyrosine and acidic amino acids (aspartate and glutamate), containing 116 basic residues (102 histidine (H), 9 lysine (K) and 5 arginine (R)). From this, a recombinant variant may be created through one or more expression, purification and processing steps that do not involve irreversible enzymatic crosslinking (that places limits on the reconfigurability of the resulting biomaterial), but rather through the interaction of oppositely charged polyelectrolytes. For example, the purified Nvjp-1 protein may be cationized in order to increase its overall positive charge compared to its natural state. From there, it can be formed into hydrogels with tunable properties. In one form, the recombinant protein can be complexated through interaction with anionic surfactant such as an alkyl ether sulfonate (AES). Thus, by electrostatically conjugating the recombinant Nvjp-1 to the anionic surfactant, a PESC in the form of a stable protein ionic liquid is created which modulates the rheological behavior of the biomaterial, specifically by imparting LLPS properties that can be used for various absorption operations, such as the ones disclosed herein regarding PFAS absorption. Significantly, the liquid remains stable, even with water addition.

Noting that the pKa of histidine is about 6.0, and that this corresponds to the pH where the number of protonated and unprotonated (neutral) histidines are equal, molecular dynamic calculations have shown that at a pH of 5, 80% of the Nvjp-1 histidines are protonated. Consequently, upon solubilization of Nvjp-1 in 10 μM hydrochloric acid (pH of 5), the protein becomes cationized, which in turn can form electrostatic interaction with the anionic polymer surfactant of poly(ethylene glycol) 4-nonylphenyl 3-sulfopropyl ether.

Figure 2B:
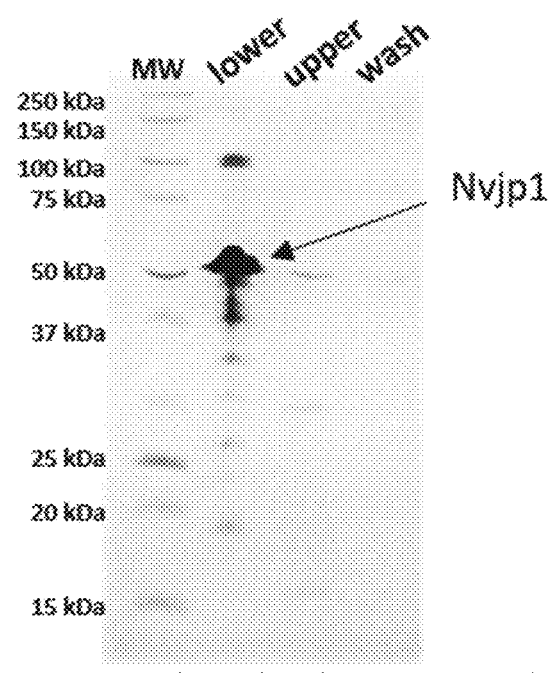
Figure 2C:
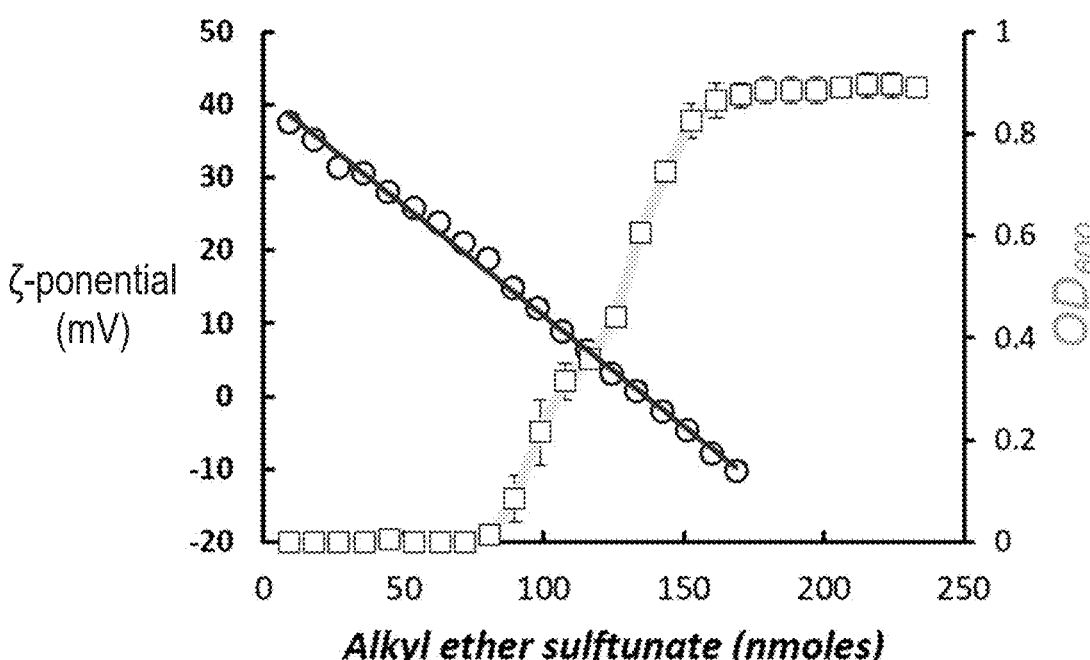

Referring next to FIGS. 2A through 2C, a series of biomaterial processing steps used to wrap the cationized protein with an anionic surfactant are shown. Referring with particularity to FIG. 2A, the construction of an LLPS Nvjp-1 and surfactant complex includes expressing and purifying the Nvjp-1 protein into a recombinant form. Upon addition of the anionic surfactant, the Nvjp-1 solution becomes turbid. Under gravimetric forces, this turbid complex separates into stable liquid-liquid two phase material consisting of Nvjp-1 condense (lower) and dilute (upper) phase liquids that are referred to herein as the first liquid and second liquid, respectively.

Referring with particularity to FIG. 2B in conjunction with the two-phase complex of FIG. 2A, the lower (that is to say, the dense coacervate) phase liquid is rich in Nvjp-1 protein, while the upper (that is to say, less dense) phase liquid is a dilute solution with little or no Nvjp-1 protein. The second liquid can be replaced multiple times to wash the dense coacervate of the first liquid; however, the Nvjp-1 protein remains in the lower portion and will not migrate into the upper portion that corresponds to the second liquid. In addition, the application of a Coomassie dye to stain the protein after gel electrophoresis (SDS-PAGE) shows that most of the Nvjp-1 protein remains within the coacervate phase that corresponds to the first liquid.

Referring with particularity to FIG. 2C, adding AES to an Nvjp-1 solution in the manner of FIG. 2A causes changes in the electrokinetic (i.e., zeta) potential and turbidity of the solution, which in turn leads to the formation of the PESC. As can be seen in FIG. 2C, an optical density measurement at 600 nm reaches a maximum around charge neutrality. In other words, in order to balance charges and produce a neutral protein salt through electrostatic complexation, the zetapotential of Nvjp-1 upon titration with the anionic surfactant was measured and determined to balance charges and reach charge neutrality when about 122.8 moles of anionic surfactant make complexation per each mole of Nvjp-1 protein. Thus, as alkyl ether sulfonate levels increase in the presence of Nvjp-1, the net charge of the protein decreases due to neutralization of the histidines by the surfactant. By the time the net charge of the protein reaches zero, a significant portion of the protein-surfactant complex has phase separated, as measured by the solution turbidity, $OD_{600}$.

Referring next to FIGS. 3A through 3D, the characterization of a phase-separated Nvjp-1 and surfactant complex in presence and absence of various transition metals is shown. Significantly, changes in LCST behavior (that is to say, at temperatures below which the system is completely miscible in all proportions) are identified for various temperature time and metal ions. This temperature can be used in applications to remove the toxic from PESC.

Figure 3A:
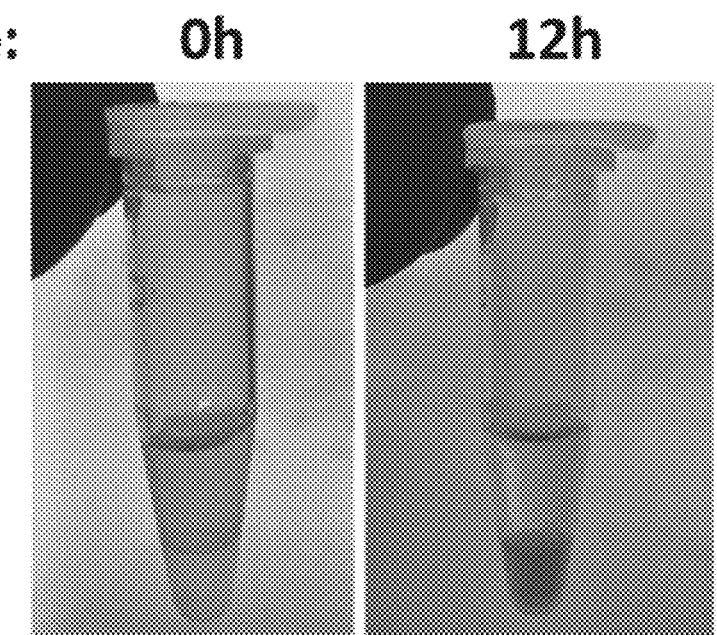
FIGS. 3A through 3D depict lower critical solution temperature (LCST) behavior for various temperature, time and metal ions of one embodiment of the phase-separated Nvjp-1 and surfactant complex of the present disclosure.

Referring with particularity to FIG. 3A, divalent metal cations such as $Ni^{2+}$, $Cu^{2+}$ and $Zn^{2+}$ have been identified as a molecular tool to control the assembling, disassembling and reassembling of histidine-rich protein materials at the nanoscale level. For example, while the reversible sclerotization of Nvjp-1 hydrogels may be induced by divalent $Zn^{2+}$ cations through the formation of coordinate crosslinks, the present figures show the effects of other metal cations on the Nvjp-1/surfactant coacervate. In particular, acetate salts of $Na^+$, $Ni^{2+}$, $Cu^{2+}$ and $Zn^{2+}$ were added to the upper (that is to say, dilute or second) phase of the LLPS complex. A schematic illustration of absorption over time using one of these, copper acetate ($Cu(OAc)_2$), is shown. As can be seen, the incubation with the divalent metal salts leads to accumulation of a metal cation in the lower (that is to say, condense or first) phase which—as previously mentioned—corresponds to the first liquid that is rich in Nvjp-1. Thus, the metal cations have a tendency to partition in the lower condense phase rather than upper dilute phase. Significantly, interaction of metal cation with the Nvjp-1 and surfactant coacervate (also referred to herein as Nvjp-1 and surfactant complex) phase causes changes in the rheological properties of such phase.

Figure 3B:
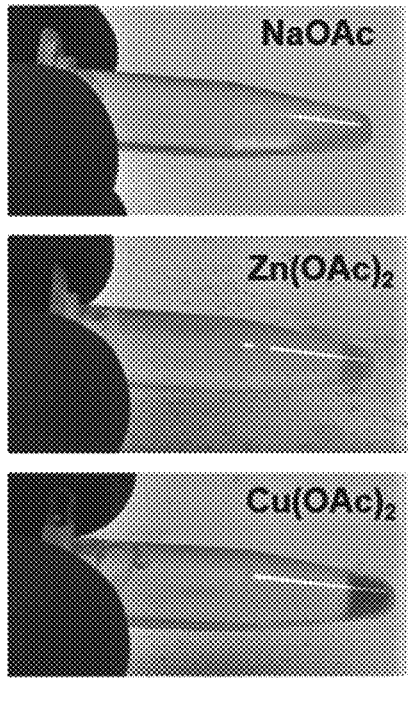

Referring with particularity to FIG. 3B, the viscosity of the Nvjp-1 and surfactant complex increases in the presence of metal cations for zinc and copper, thereby slowing or preventing flow of the lower phase when the tube containing the coacervate is tilted. Without wishing to be bound by theory, the authors of the present disclosure note that the changes in rheological properties of the coacervate is induced by metal cation, not the acetate anion, as the presence of NaOAc does not increase the viscosity of the coacervate phase.

Figure 3C:
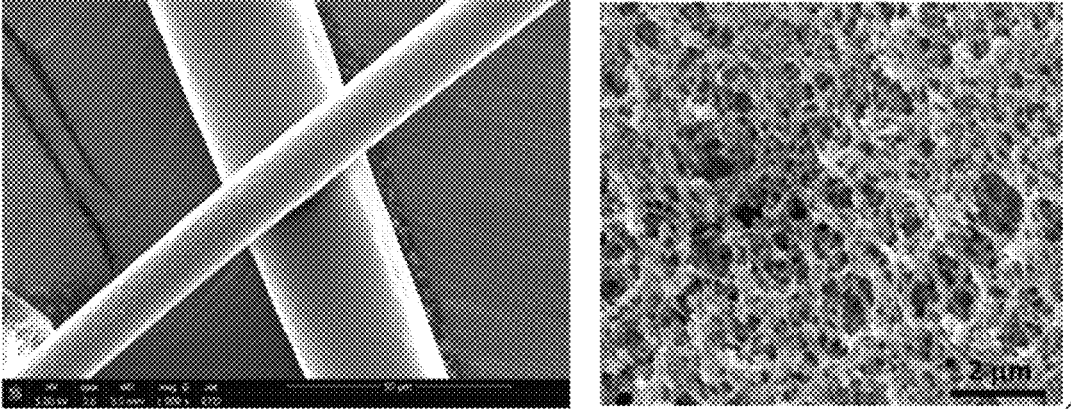

Referring with particularity to FIG. 3C, scanning electron microscope (SEM) images of a structural assembly of the Nvjp-1 and surfactant complex in the presence of $Cu(OAc)_2$ and $Zn(OAc)_2$ are shown. In particular, the assembly of protein coacervate at a microscale level depends on the type of metal cation that was interacted with the Nvjp-1 and surfactant coacervate. As can be seen in the left side of FIG. 3C, the presence of copper acetate permits the spinning of Nvjp-1 fibers out of the Nvjp-1 and surfactant complex, while the right side of FIG. 3C shows that in the presence of zinc acetate, a porous membrane may be cast.

Figure 3D:
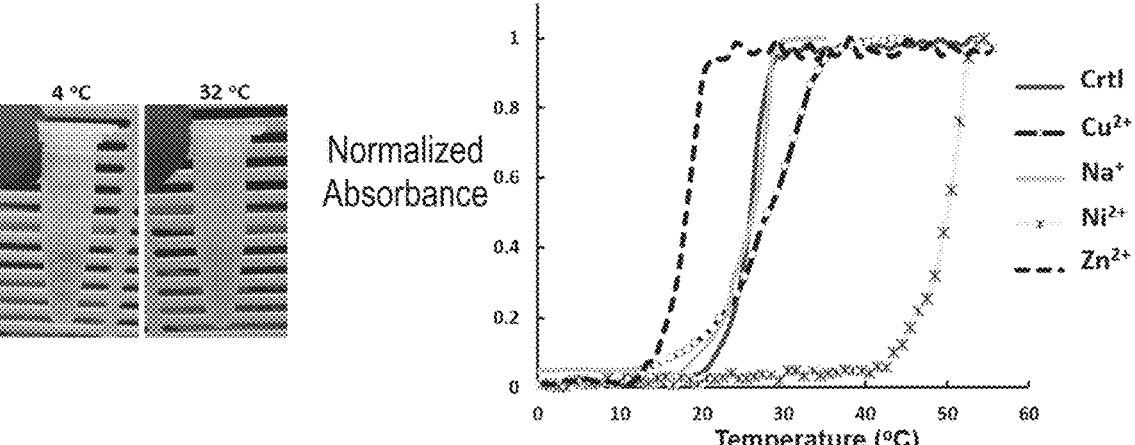

Referring with particularity to FIG. 3D, changes in the LCST behavior and clouding point with the Nvjp-1 and surfactant complex in the presence of different metal cations as a way to understand the thermally induced phase transition of PESCs are shown. This thermoresponsive behavior suggests that the LCST behavior of PESCs could occur only under certain situations, such as decreasing the dielectric constant of the solvent and increasing the solvent-polymer interaction parameter with rising temperature. In the present case, the observed clouding of the complexation with rising temperature indicates the existence of LCST. FIG. 3D depicts the LCST behavior in the presence of different metal cations such that an increase or decrease in the clouding point may be based on the type of metal cation that was interacted with the coacervate phase. As shown, the zinc and nickel cations have the most extreme effect on shifting the cloud point related to LCST of the Nvjp-1 and surfactant coacervate. For example, in the control sample, where there is an absence of a metal cation, the cloud point is at 25° C., while in the presence of a zinc cation the cloud point drops to 15° C. and in the presence of a nickel cation this point increases to 50° C. Significantly, the LCST shows that— depending on the metal cation—not only does the LCST change, but so does the amount of absorption to the lower phase first liquid which is rich in the recombinant Nvjp-1 protein.

Figure 4:
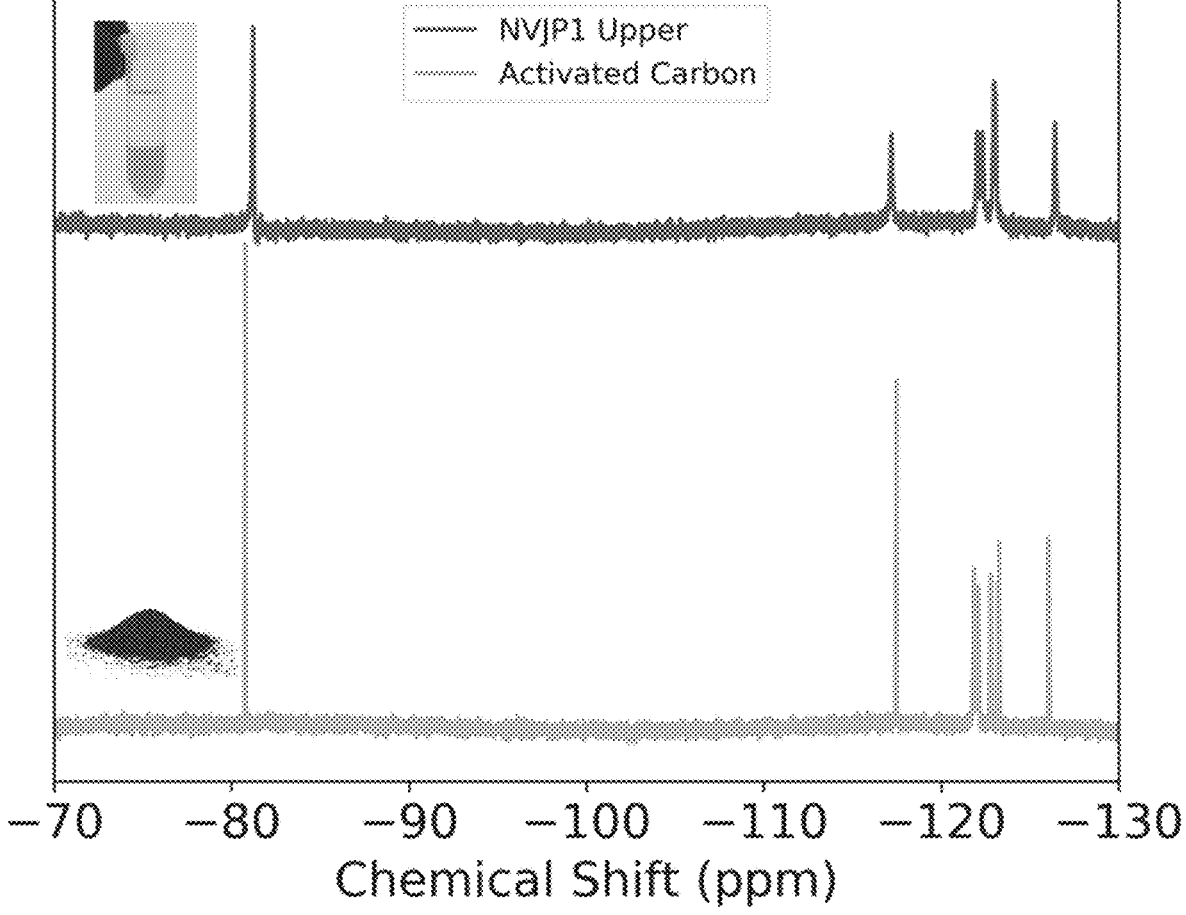
FIG. 4 depicts a nuclear magnetic resonance (NMR) spectrum of a saturated perfluorooctanoic acid (PFOA) solution when treated with equal dry mass of the recombinant Nvjp-1/surfactant complex compared to activated carbon.

Referring next to FIG. 4, the authors of the present disclosure conducted experiments of a saturated PFOA solution (which is a very common form of PFAS and is often referred to as C8). A fluorine-19 ($^{19}$F) NMR spectrum of signal intensity versus chemical shift is an overlay of the Nvjp-1 and surfactant complex (shown as the upper line) and the activated carbon (shown as the lower line). Significantly, the signal intensity, which is indicative of the amount of the absorbed PFOA species, shows that a water sample that was treated with the Nvjp-1 and surfactant complex has fewer than two-thirds of the contaminants than a comparable water sample that was treated with activated carbon for the same length of time. In particular, the integrated intensities of the $CF_3$ peak at about –80 ppm showed that the Nvjp-1 and surfactant coacervate is 1.24 times more efficient in removal of PFOA from the aqueous solution than the activated carbon. Significantly, even at lower concentrations of toxic substances, the performance of the Nvjp-1 and surfactant complex is greater than that of the activated carbon the latter of which is known to have limited performance at relatively low concentrations of toxic ions.

Referring next to FIGS. 5A through 5D, results showing the efficacy of the Nvjp-1 and surfactant complex as a protein-based absorbent are shown. Referring with particularity to FIG. SA, because of the abundant hydrophilic and hydrophobic domains in dense molecular environments, the application of various coacervate complexes that can act as a sorbent for the removal of toxic materials to various scenarios is possible, regardless of whether they are hydrophobic, hydrophilic or amphiphilic. As previous disclosed, the Nvjp-1 and surfactant complex disclosed herein works as an absorbent for removal of—in addition to PFAS-based materials—heavy metal ions such as $Ni^{2+}$, $Cu^{2+}$ and $Zn^{2+}$, and as such can be applied towards decontamination of water for toxic substances containing these species. As can be seen from these particular examples, after a mixing and spin-down operation, the Nvjp-1 and surfactant coacervate may be used to absorb and capture melanin, melanin ionic liquids (IL) and gold nanoparticles, as well as ferritin ionic liquid (not shown).

Figure 5A:
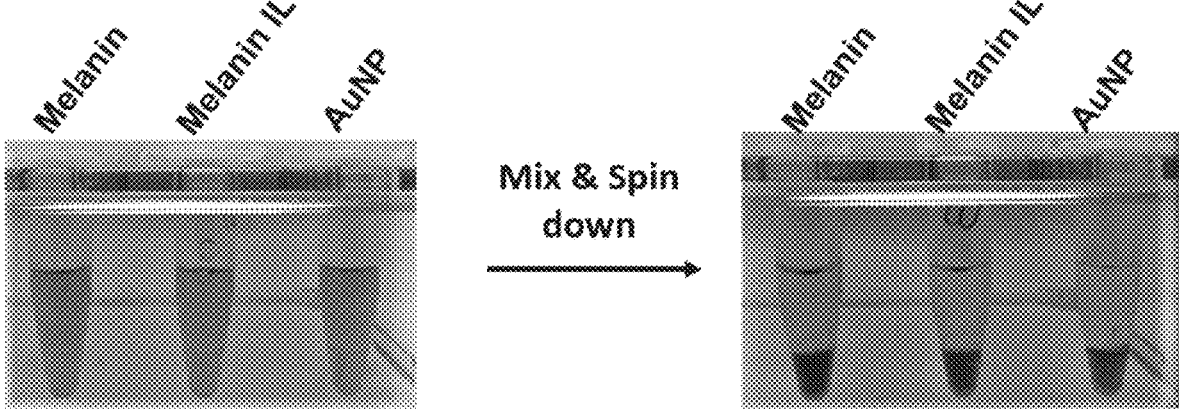
FIGS. 5A through 5D depict how coacervate complexes according to one embodiment of the phase-separated Nvjp-1 and surfactant complex of the present disclosure perform as a sorbent for the removal of toxic materials.
Figure 5B:
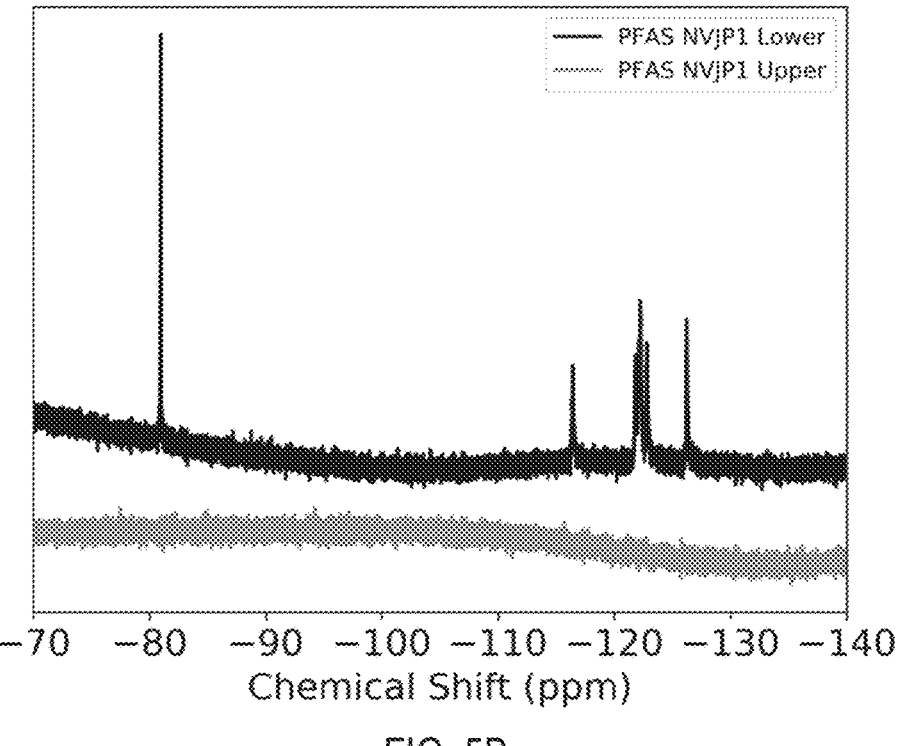

Referring with particularity to FIG. 5B, the accumulation of the PFOA of FIG. 4 in the lower and upper phases (that is to say, the first and second liquids) of the Nvjp-1 and surfactant coacervate is revealed using the $^{19}$F NMR. Of note is that the effective removal of PFOA from the upper phase and accumulation of PFOA in the lower phase. This validates the observations made in conjunction with FIG. 4.

Figure 5C:
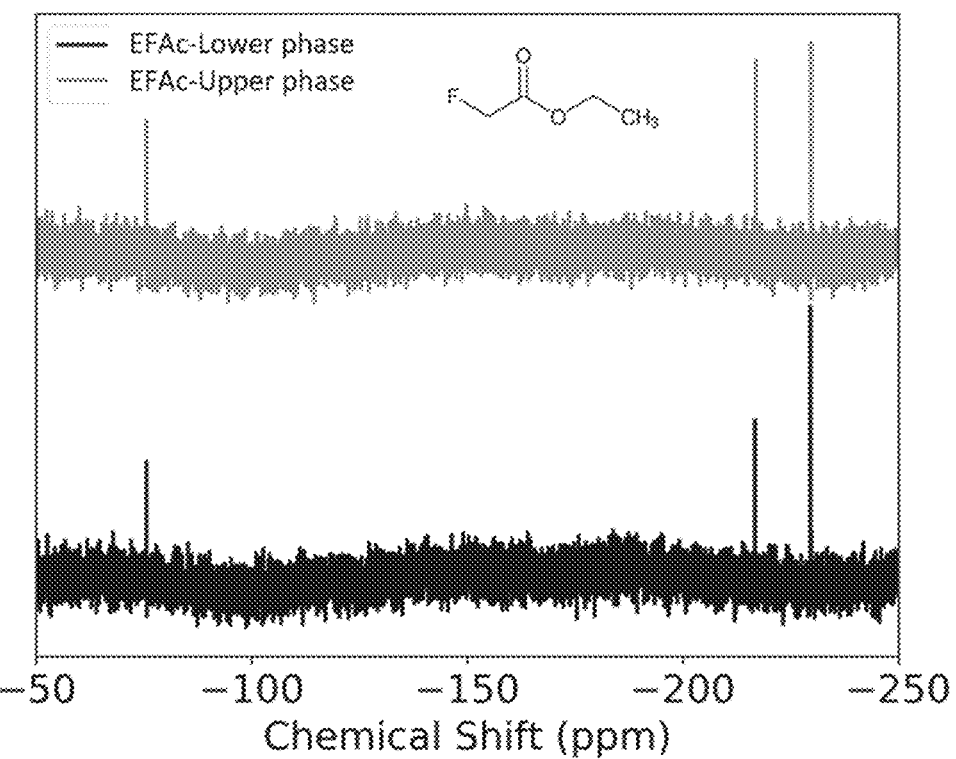
Figure 5D:
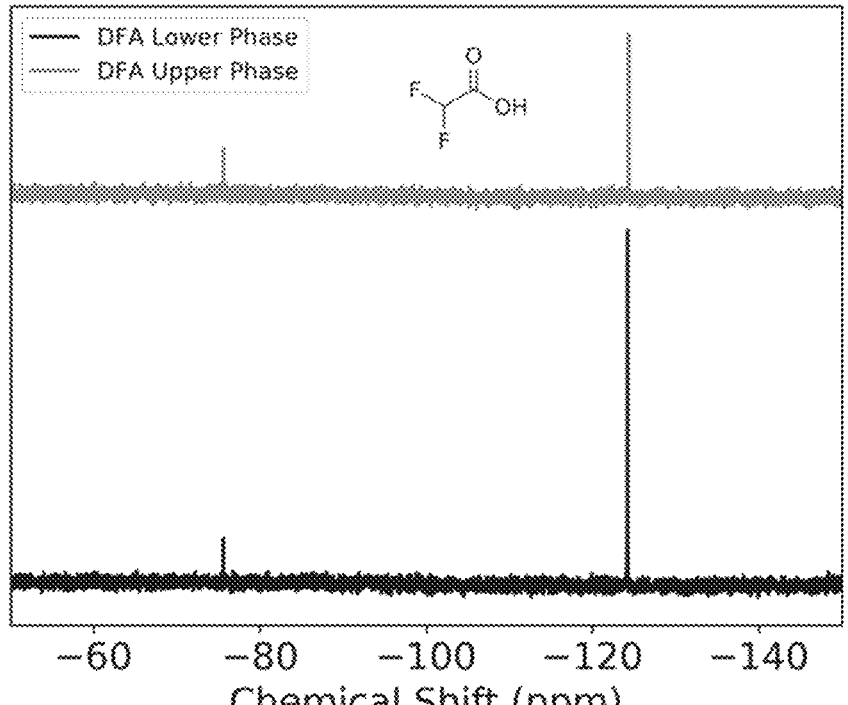

Referring with particularity to FIGS. 5C and 5D, the authors of the present disclosure have noticed that the removal of short-chain PFAS may be more challenging since the adsorption capacity of short-chain PFAS compounds is lower than that observed for their long-chain counterparts. In the present case, EFAc (FIG. 5C) and difluoro acetic acid (DFA, FIG. 5D) were selected as short-chain PFAS proxies in order to assess their adsorption capacity to the Nvjp-1 and surfactant coacervate disclosed herein. As can be seen, the capture is less effective than that of the long chain PFAS compounds.

Figure 6A:
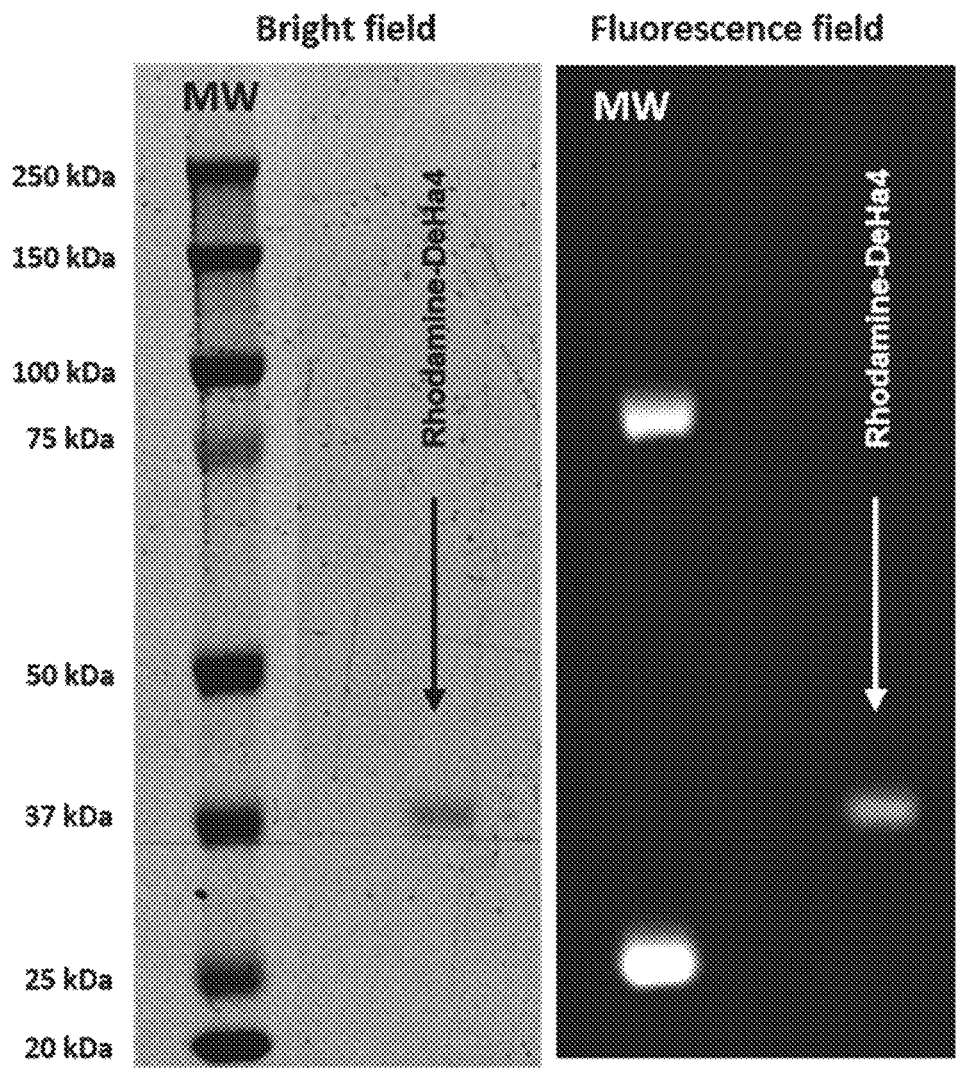
FIGS. 6A and 6B depict localization of dehalogenase enzymes within one embodiment of the phase-separated Nvjp-1 and surfactant complex of the present disclosure.
Figure 6B:
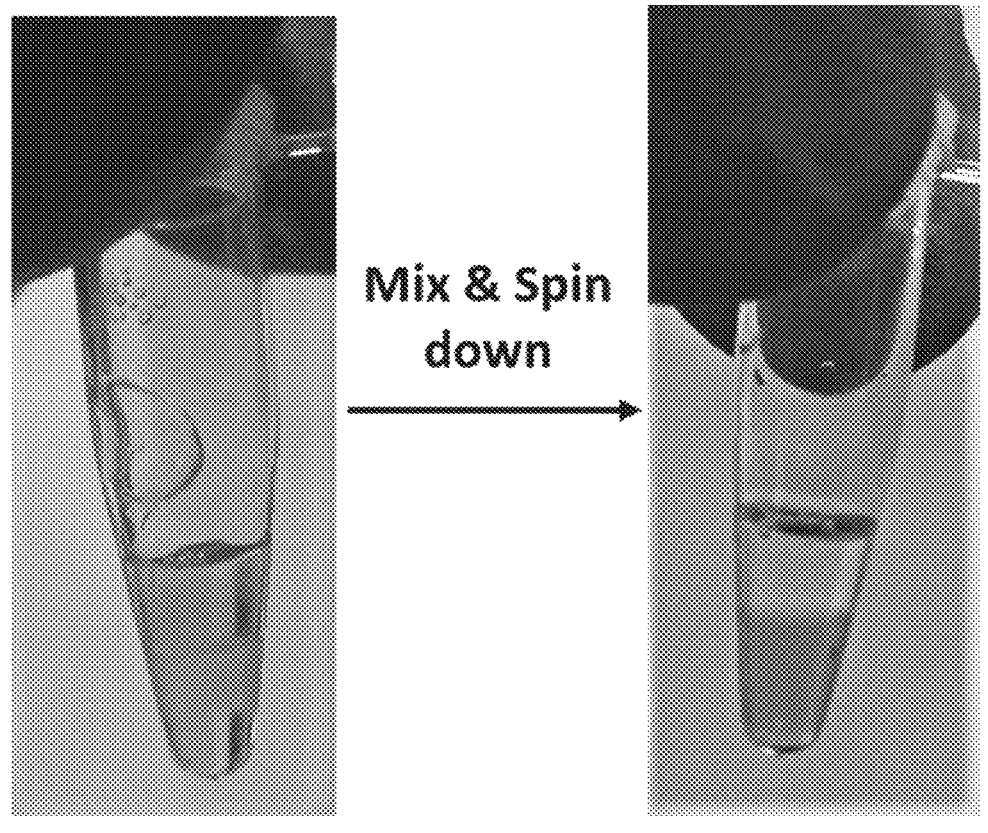

Referring next to FIGS. 6A and 6B, because enzymes play important biological roles by accelerating the rates of diverse types of biological reactions, the authors of the present disclosure have determined that using enzymatic processes may be useful in recycling and reusing the Nvjp-1 and surfactant coacervate. In particular, by using cellular condensates—the phase-separated concentrates of nucleic acids from proteins—the activities of biological enzymes can be regulated, particularly by selectively promoting certain biochemical processes that may otherwise be slow or thermodynamically unfavorable. For example, by concentrating the substrate concentration within the coacervate phase, enzyme enrichment or the use of tailored substrates can lead to increased specificity that in turn can alter the activation barrier and performance of enzymes. The authors took a dehalogenase enzyme (DeHa4) that they developed and evaluated it for its activity when immobilized within the Nvjp-1 and surfactant coacervate. Referring with particularity to FIG. 6A, the enzyme was fluorescently labeled using rhodamine to determine if the enzyme would partition within the coacervate phase. On the left side of the figure, the bright field depicts the enzyme next to the molecular weight (MW) ladder that can be used to ensure accuracy in enzyme size, whereas the fluorescence field is showing that the protein is labelled properly and can be fluoresced Referring with particularity to FIG. 6B, upon addition of the labeled DeHa4 enzyme to the coacervate followed by mixing and a spin-down, the enzyme is absorbed, collecting predominantly in the (lower) first liquid; this can be readily seen by comparing the sample to one that contained water (not shown) where the enzyme remains evenly dispersed throughout one-phase liquid of the sample.

Figure 7:
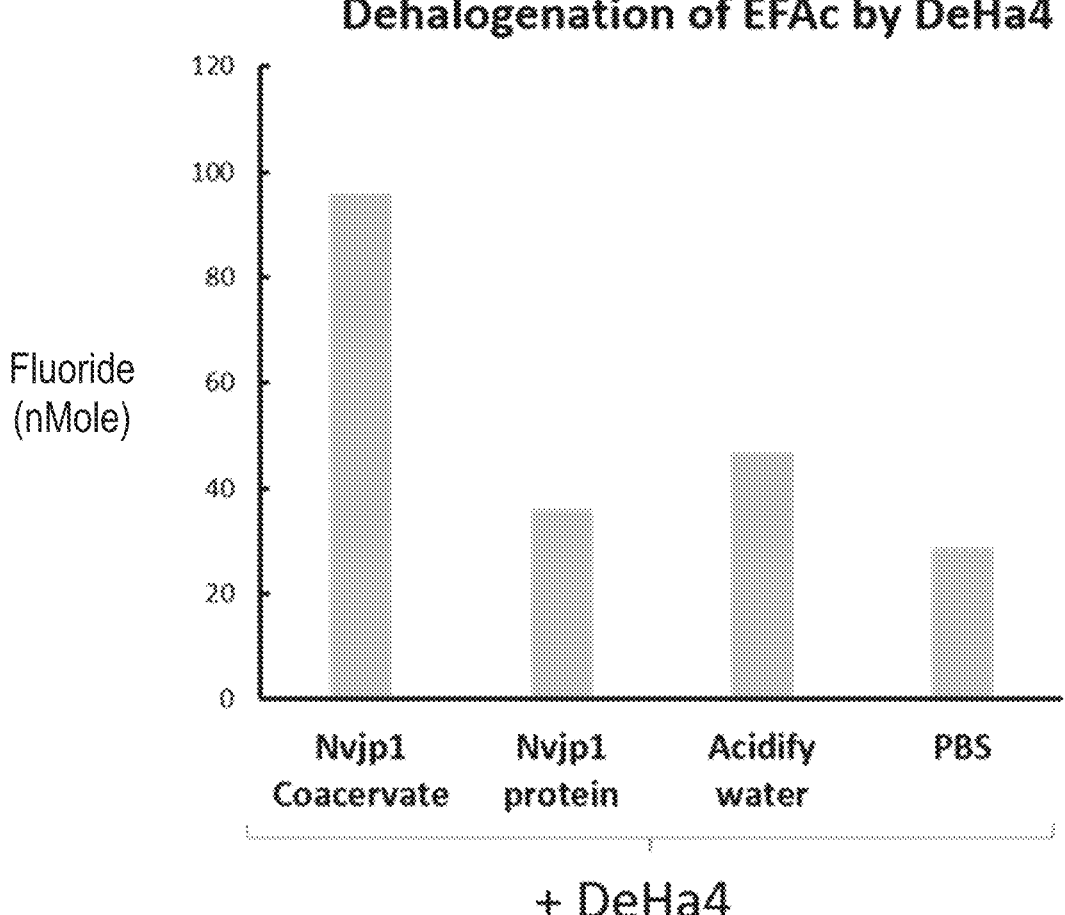
FIG. 7 depicts rates of dehalogenation of an ethylfluoro acetate (EFAc) with the enzyme of FIGS. 6A and 6B.

Referring next to FIG. 7, the DeHa4 enzyme stay active while it is absorbed within the Nvjp-1 and surfactant coacervate phase. Other environments are shown for comparison, including an untreated Nvjp-1 protein, acidified water and a phosphate buffered saline (PBS) solution. The catalytic rate of DeHa4 enzyme within the coacervate phase may increase or not depending to the type of substrate; significantly, the enzyme remains active, even in this surfactant-rich environment. Without wishing to be bound by theory as to how the mechanism of action of the dehalogenase takes place, the authors of the present disclosure have determined that the enzyme leads to defluorination of the ethyl acetate substrate, resulting in a free fluoride ion that is detected electrochemically with a fluoride probe.

Within the present disclosure, while environmental remediation in the form of contaminated groundwater and soil cleanup is emphasized, it will be appreciated that the compounds disclosed herein, such as ones using recombinant IDPs that have been complexed with anionic surfactants, may be used for other procedures as well, including bioleaching and various catalytic-based operations, and that all such operations are deemed to be within the scope of the present disclosure. Significantly, the resulting LLPS material disclosed herein is able to concentrate solutes, such as metal ions and toxic chemicals that may help in such bioleaching, catalysis and environmental remediation efforts. The authors of the present disclosure note with particularity that while the present disclosure emphasizes the removal of one particular toxic material (PFAS), it will be appreciated that the absorbents, systems and methods disclosed herein are equally applicable to—and may be tailored toward—other toxic materials such as industrial dyes, nanoparticles and heavy metals, and that all such uses are within the scope of the present disclosure.

Within the present disclosure, contaminated groundwater may include—either partly or completely—wastewater, such as that which arises out of one or more industrial or chemical processes. In situations where specificity or similarity between the two is intended, it will be apparent from the context.

Throughout the present disclosure, one particular protein (Nvjp-1) has been discussed that can be used as a precursor to the formation of the complexated biomolecules disclosed herein; however, it will be appreciated that the cost of using natural proteins such as this could be reduced for manufacturing scale-up or the like. As such, adjustments to such precursor may be made, including the use of various amino acids, peptides, other proteins or the like as a way to adjust the formula for specific activations, applications that result in a scalable chemical formulation (such as a random heteropolymer with differing ratios of amino acids) with comparable efficacy. Variants such as this are deemed to be within the scope of the present disclosure. In one form, the efficacy of random heteropolymers can be validated through the use of N-carboxyanhydride (NCA) versions of the four highest represented amino acids (glycine, histidine, tyrosine and aspartate) present in Nvjp-1. The NCA versions of each amino acid will be added together at the same molar percentage that they are represented in Nvjp-1. Moreover, using ring-opening polymerization techniques will create polydisperse polypeptide chains with randomly variated amino acids in a one-pot synthesis regime. This in turn allows for scaled-up production of an Nvjp-1-like polypeptide that will be converted to the coacervate through electrostatic conjugation with alkyl ether sulfonate.

Within the present disclosure, one or more of the following claims may utilize the term "wherein" as a transitional phrase. For the purposes of defining features discussed in the present disclosure, this term is introduced in the claims as an open-ended transitional phrase that is used to introduce a recitation of a series of characteristics of the structure and should be interpreted in like manner as the more commonly used open-ended preamble term "comprising" and its variants that do not preclude the possibility of additional acts or structures.

Within the present disclosure, terms such as "preferably", "generally" and "typically" are not utilized to limit the scope of the claims or to imply that certain features are critical, essential, or even important to the disclosed structures or functions. Rather, these terms are merely intended to highlight alternative or additional features that may or may not be utilized in a particular embodiment of the disclosed subject matter. Likewise, it is noted that the terms "substantially" and "approximately" and their variants are utilized to represent the inherent degree of uncertainty that may be attributed to any quantitative comparison, value, measurement or other representation. As such, use of these terms represents the degree by which a quantitative representation may vary from a stated reference without resulting in a change in the basic function of the subject matter at issue.

Within the present disclosure, the use of the prepositional phrase "at least one of" is deemed to be an open-ended expression that has both conjunctive and disjunctive attributes. For example, a claim that states "at least one of A, B and C" (where A, B and C are definite or indefinite articles that are the referents of the prepositional phrase) means A alone, B alone, C alone, A and B together, A and C together, B and C together, or A, B and C together.

Within the present disclosure, the following claims are not intended to be interpreted based on 35 USC 112(f) unless and until such claim limitations expressly use the phrase "means for" or "steps for" followed by a statement of function void of further structure. Moreover, the corresponding structures, materials, acts and equivalents of all means or step plus function elements in the claims below are intended to include any structure, material or act for performing the function in combination with other claimed elements as specifically claimed.

Within the present disclosure, the singular forms "a," "an" and "the" include plural references unless the context clearly dictates otherwise. The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

For the recitation of numeric ranges herein, each intervening number therebetween with the same degree of precision is explicitly contemplated. For example, for the range of 6 to 9, the numbers 7 and 8 are contemplated in addition to 6 and 9, and for the range 6.0 to 7.0, the number 6.0, 6.1, 6.2, 6.3, 6.4, 6.5, 6.6, 6.7, 6.8, 6.9 and 7.0 are explicitly contemplated.

The present description is for purposes of illustration and is not intended to be exhaustive or limited. Many modifications and variations will be apparent to those of ordinary skill in the art without departing from the scope and spirit of the present disclosure. Aspects of the present disclosure were chosen and described in order to best explain the principles and practical applications, and to enable others of ordinary skill in the art to understand the subject matter contained herein for various embodiments with various modifications as are suited to the particular use contemplated.

Unless otherwise defined, all technical and scientific terms used herein that relate to materials and their processing have the same meaning as commonly understood by one of ordinary skill in the art. In case of conflict, the present document, including definitions, will control.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method of removing a substance from soil or groundwater, the method comprising:
    receiving a polyelectrolyte-surfactant complex comprising a cationized protein that has undergone electrostatic conjugation with an anionic surfactant such that the polyelectrolyte-surfactant complex has a first liquid and a second liquid such that a complexated protein is present in the first liquid in a greater concentration than in the second liquid;

combining the polyelectrolyte-surfactant complex with at least one of the soil and the groundwater such that the substance contained therein absorbs into the complexated protein within the first liquid while the second liquid remains predominantly in contact with the groundwater or soil; and separating the first liquid and the substance extracted thereto from the second liquid.

2. The method of claim 1, wherein the substance comprises at least one fluorinated substance.

3. The method of claim 2, wherein the at least one fluorinated substance comprises polyfluoroalkyl and perfluoroalkyl substances.

4. The method of claim 1, wherein the anionic surfactant comprises an alkyl ether sulfonate.

5. The method of claim 1, wherein the cationized protein comprises an intrinsically disordered protein.

6. The method of claim 5, wherein the intrinsically disordered protein comprises purified Nvjp-1.

7. The method of claim 1, wherein the polyelectrolyte-surfactant complex contains a metal salt.

8. The method of claim 7, wherein the metal salt comprises a copper-based metal salt.

9. The method of claim 8, wherein the copper-based metal salt comprises copper acetate.

10. The method of claim 1, further comprising degrading the toxic substance that is adhered to the first liquid.

11. The method of claim 1, further comprising recycling the first liquid.

12. The method of claim 11, wherein the recycling comprises using an enzyme-based material to react with the polyelectrolyte-surfactant complex.

13. The method of claim 1, further comprising enclosing the separated first liquid and the extracted substance in a hermetically-sealable container.

14. The method of claim 1, further comprising extracting the complexated protein from the extracted substance after separating the first liquid from the second liquid.

15. The method of claim 1, wherein the substance comprises at least one of industrial dyes, nanoparticles and heavy metals.

* * * * *